United States Patent
Fox et al.

(10) Patent No.: US 8,002,777 B2
(45) Date of Patent: Aug. 23, 2011

(54) INSTRUMENTATION AND METHOD FOR IMPLANTING A CURVED STEM TIBIAL TRAY

(75) Inventors: Duke A. Fox, Winona Lake, IN (US);
Robert Metzger, Wakarusa, IN (US);
Jacy C. Hoeppner, Warsaw, IN (US);
Richard Detlefsen, Fort Wayne, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 625 days.

(21) Appl. No.: 12/052,206

(22) Filed: Mar. 20, 2008

(65) Prior Publication Data

US 2008/0183177 A1    Jul. 31, 2008

Related U.S. Application Data

(63) Continuation-in-part of application No. 11/149,495, filed on Jun. 9, 2005, now abandoned.

(51) Int. Cl.
*A61B 17/58* (2006.01)
*A61B 17/60* (2006.01)
*A61F 2/00* (2006.01)

(52) U.S. Cl. ........................................................ 606/88

(58) Field of Classification Search ............... 623/20.14, 623/20.21, 20.32, 20.34; 606/86 R, 87–88, 606/96, 98
See application file for complete search history.

(56) References Cited

U.S. PATENT DOCUMENTS

| | | | |
|---|---|---|---|
| 347,580 A | 8/1886 | Dean | |
| 1,011,628 A | 12/1911 | Klein | |
| 1,529,075 A | 3/1925 | McIntyre | |
| 1,624,051 A | 4/1927 | Hansen | |
| D162,858 S | 4/1951 | McGlinchey | |
| 2,804,683 A | 9/1957 | Hammond | |
| D184,451 S | 2/1959 | Mullin | |
| 3,109,334 A | 11/1963 | Miranda | |
| 3,203,285 A | 8/1965 | Schmidt | |
| D230,098 S | 1/1974 | Rylee, II | |
| 4,211,228 A | 7/1980 | Cloutier | |
| 4,822,362 A | 4/1989 | Walker et al. | |
| 4,938,769 A | 7/1990 | Shaw | |
| 5,007,933 A | 4/1991 | Sidebotham et al. | |
| 5,089,003 A * | 2/1992 | Fallin et al. | 606/85 |
| 5,282,866 A | 2/1994 | Cohen et al. | |
| 5,356,414 A | 10/1994 | Cohen et al. | |
| 5,358,530 A | 10/1994 | Hodorek | |
| 5,413,605 A | 5/1995 | Ashby et al. | |
| 5,462,549 A | 10/1995 | Glock | |
| 5,609,641 A | 3/1997 | Johnson et al. | |
| 5,609,642 A | 3/1997 | Johnson et al. | |
| 5,630,820 A | 5/1997 | Todd | |
| 5,683,469 A | 11/1997 | Johnson et al. | |
| 5,690,636 A * | 11/1997 | Wildgoose et al. | 606/88 |
| 5,702,463 A | 12/1997 | Pothier et al. | |
| 5,733,290 A | 3/1998 | McCue et al. | |
| 5,782,920 A | 7/1998 | Colleran | |
| 5,871,543 A | 2/1999 | Hofmann | |

(Continued)

*Primary Examiner* — Thomas C Barrett
*Assistant Examiner* — Sameh Boles
(74) *Attorney, Agent, or Firm* — Harness, Dickey

(57) ABSTRACT

A punch assembly for preparing a tibia bone for a prosthesis includes a static component configured to be supported by the tibia bone and a dynamic component that includes a punch having a stem. The dynamic component is supported for movement relative to the static component along a generally arcuate path to prepare an aperture having an arcuate contour in the tibia bone. A method of preparing a tibial aperture for is also disclosed.

18 Claims, 13 Drawing Sheets

U.S. PATENT DOCUMENTS

| | | |
|---|---|---|
| D406,519 S | 3/1999 | White |
| 5,906,144 A | 5/1999 | Staviski et al. |
| 5,925,049 A | 7/1999 | Gustilo et al. |
| 5,980,526 A | 11/1999 | Johnson et al. |
| 6,139,581 A | 10/2000 | Engh et al. |
| 6,159,216 A | 12/2000 | Burkinshaw et al. |
| 6,162,255 A | 12/2000 | Oyola |
| 6,165,223 A | 12/2000 | Metzger et al. |
| 6,165,224 A | 12/2000 | Tornier |
| 6,258,127 B1 | 7/2001 | Schmotzer |
| 6,319,283 B1 | 11/2001 | Insall et al. |
| 6,355,045 B1 | 3/2002 | Gundlapalli et al. |
| 6,379,388 B1 | 4/2002 | Ensign et al. |
| 6,413,279 B1 | 7/2002 | Metzger et al. |
| 6,428,577 B1 | 8/2002 | Evans et al. |
| 6,660,039 B1 | 12/2003 | Evans et al. |
| 6,679,888 B2 * | 1/2004 | Green et al. ................ 606/86 R |
| 6,869,448 B2 | 3/2005 | Tuke et al. |
| 6,942,670 B2 | 9/2005 | Heldreth et al. |
| 7,422,605 B2 | 9/2008 | Burstein et al. |
| 7,766,969 B2 * | 8/2010 | Justin et al. ................ 623/20.15 |
| 2004/0102785 A1 | 5/2004 | Hodorek et al. |
| 2005/0015153 A1 | 1/2005 | Goble et al. |
| 2006/0058803 A1 | 3/2006 | Cuckler et al. |
| 2006/0116772 A1 * | 6/2006 | Haidukewych ............ 623/20.34 |
| 2006/0142869 A1 | 6/2006 | Gross |
| 2006/0265079 A1 | 11/2006 | D'Alessio |
| 2007/0010890 A1 | 1/2007 | Collazo |
| 2008/0183177 A1 | 7/2008 | Fox et al. |
| 2008/0221586 A1 * | 9/2008 | Garcia-Bengochea et al. ............................ 606/108 |
| 2009/0062806 A1 | 3/2009 | Scott et al. |

* cited by examiner

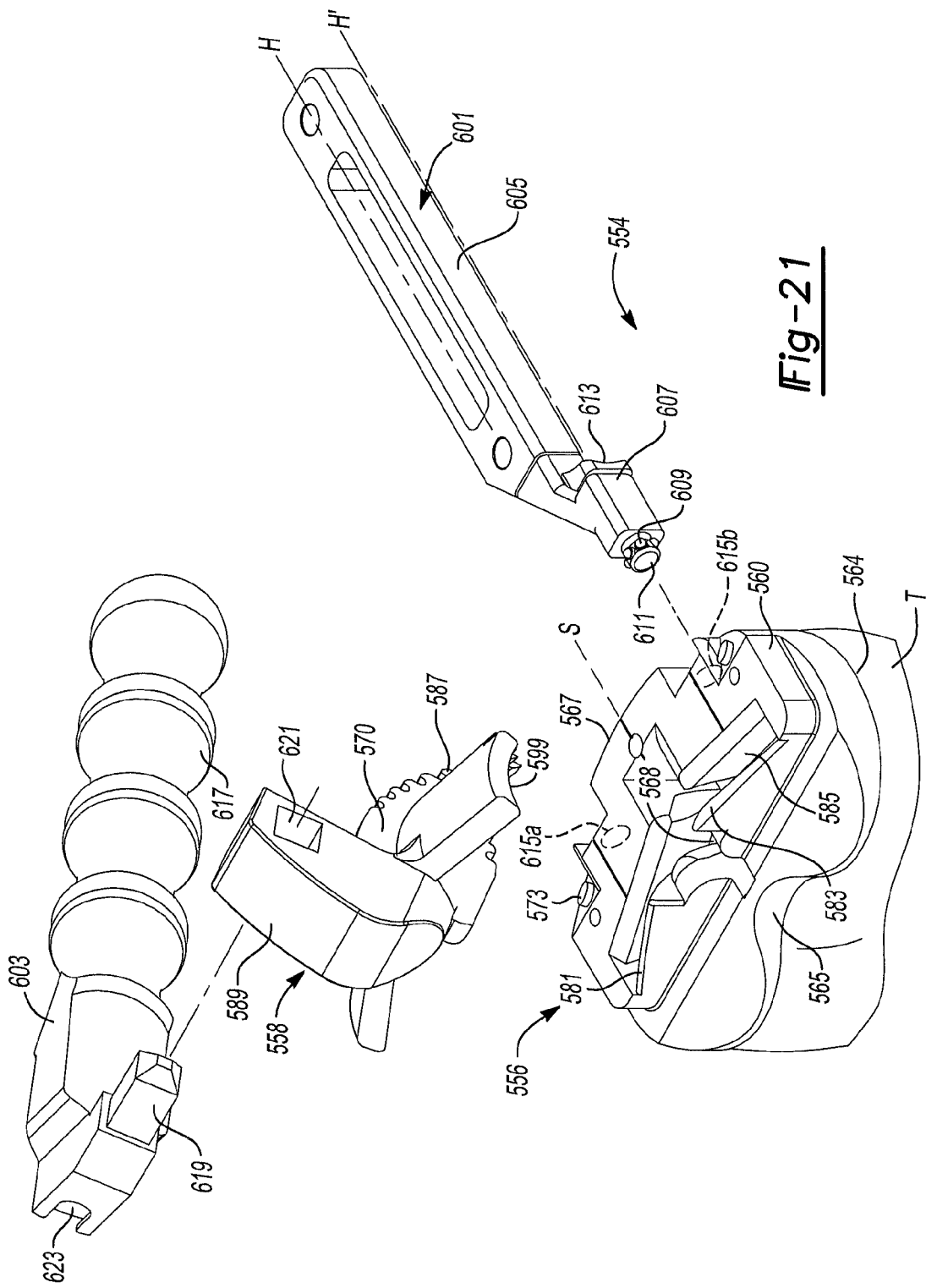

INSTRUMENTATION AND METHOD FOR IMPLANTING A CURVED STEM TIBIAL TRAY

CROSS REFERENCE TO RELATED APPLICATION(S)

This application is a continuation-in-part of U.S. patent application Ser. No. 11/149,495, filed on Jun. 9, 2005, the disclosure of which is incorporated herein by reference in its entirety.

FIELD

This invention relates to tibial trays and more particularly to instrumentation and a method for implementing a curved stem tibial tray.

INTRODUCTION

The knee joint is a complex articulating structure. The knee joint includes a femur, which articulates with a tibia, and a patella, which acts as a protective shield for the articulating knee joint. The knee joint also includes soft tissue ligaments that extend on the medial and lateral side of the knee joint, and are generally referred to as collateral ligaments. The soft tissue ligaments which cross within the knee joint are generally referred to as an anterior cruciate ligament and a posterior cruciate ligament.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

Typically the tibial component includes a substantially planar platform-like tibial tray and an inferiorly extending tibial stem. The tibial stem is adapted to be received in a corresponding opening made by a surgeon in the longitudinal center of the tibia. In one example, the tibial stem extends linearly from the tibial tray. Typically, the tibial stem defines a perpendicular relationship with the planar surface of the tibial tray. In some instances, it may be difficult to implant the tibial stem into the prepared tibial opening because of potential clearance issues with the distal femur and/or surrounding tissue.

Furthermore, preparing the tibia bone for implantation of the tibial component often involves the use of a punch assembly. The punch assembly typically includes a punch that is driven into the tibia to prepare and form a tibial canal. The stem of the tibial component of the prosthesis is received in the tibial canal for attachment of the tibial component to the tibia bone. In some instances, it can be difficult to operate the punch assembly because of potential clearance issues with the distal femur and/or surrounding tissue.

SUMMARY OF THE INVENTION

A punch assembly for preparing a tibia bone for a prosthesis is disclosed that includes a static component configured to be supported by the tibia bone and a dynamic component that includes a punch having a stem. The dynamic component is supported for movement relative to the static component along a generally arcuate path to prepare an aperture having an arcuate contour in the tibia bone.

In another aspect, a method of preparing a tibia bone for a prosthesis is disclosed. The method includes locating a static component of a punch assembly having a first support surface on the tibia bone. The method also includes moving a dynamic component of the punch assembly having a stem with a second support surface relative to the static component. The second support surface slides on the first support surface, and the dynamic component of the punch assembly moves along a generally arcuate path into the tibia bone to prepare an aperture having an arcuate contour in the tibia bone.

In still another aspect, a punch assembly for preparing a tibia bone for a knee joint prosthesis is disclosed. The punch assembly includes a static component configured to be supported by the tibia bone. The static component defines a passage partially defined by a first arcuate support surface that defines a generally arcuate path. The passage is further defined by a third support surface that is substantially parallel and disposed at a distance from an imaginary line that is substantially tangent to the first arcuate support surface. Furthermore, the punch assembly includes a dynamic component with a punch having a stem. The stem has a generally cruciform shape, an arcuate contour, a plurality of teeth, and a second arcuate support surface supported for sliding movement against the first arcuate support surface of the static component along the generally arcuate path to prepare an aperture having an arcuate contour in the tibia bone.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 21 is a perspective exploded view of the punch assembly of FIG. 16 in association with removably coupled handles and a tibia bone.

DETAILED DESCRIPTION OF THE PREFERRED EMBODIMENTS

The following description of the embodiment(s) is merely exemplary in nature and is in no way intended to limit the invention, its application, or uses.

Figure 1:
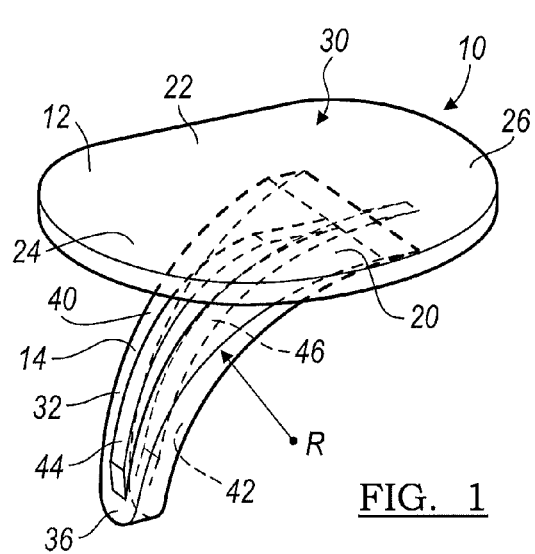
FIG. 1 is a perspective view of a tibial tray having an arcuate stem according to the present teachings.

With initial reference now to FIG. 1 a tibial component 10 is shown. The tibial component 10 generally includes a substantially planar platform-like tray 12 having a fixed, inferiorly extending tibial stem 14. The tibial stem 14 is adapted to be received in a corresponding opening made by a surgeon in the proximal tibia. As will become appreciated from the following discussion, the stem arrangement facilitates a minimally invasive implantation procedure.

For discussion purposes, the tibial component 10 will be described for use with a knee joint having a surgically resected left tibia. It is understood however that the tibial component 10 may be universal such that it may be adapted for use with a surgically resected right tibia. Likewise, the tibial component 10 may be adapted for use in either a left or right tibia. The tibial tray 12 generally defines an anterior portion 20, a posterior portion 22, a medial portion 24 and a lateral portion 26. A top surface 30 of the tibial tray 12 may be highly polished to provide a substantially smooth tibial bearing surface. While not specifically shown, a floating bearing having a substantially planar inferior bearing surface may be located above the tibial tray 12. In this way, the floating bearing may slidably move relative to the highly polished tibial bearing surface 30. It is appreciated that the tibial tray 12 may alternatively be adapted for use in a fixed bearing arrangement as will be described in relation to FIG. 6B. Likewise, the tibial tray 12 may be adapted for use in a crutiate retaining (CR) knee replacement, a posterior stabilized (PS) knee replacement and a fully constrained knee replacement.

With continued reference to FIG. 1, the tibial stem 14 defines an elongated body 32 having an arcuate contour. The tibial stem 14 extends from the anterior portion 20 of the tibial tray 12 to a distal tip 36 in a generally posterior/inferior direction defining a radius R. The elongated body 32 defines a planar medial surface 40 and a planar lateral surface 42. A medial and lateral fin 44 and 46, respectively, are arranged along the respective medial and lateral surfaces, 40 and 42. The medial and lateral fins 44 and 46 may discourage rotation of the tibial tray 14 about the stem 14 once implanted. In one example, the medial and lateral fins 44 and 46 extend generally perpendicular from the medial and lateral surfaces 40 and 42. The tibial tray 12 and tibial stem 14 may be manufactured from cobalt-chromium-molybdenum or any other suitable biocompatible material.

Figure 2A:
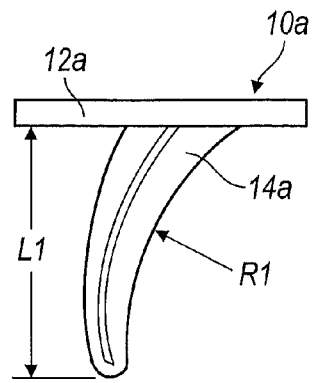
FIGS. 2A-2C are sectional views of a series of tibial trays having arcuate stems with various lengths and curvatures.
Figure 2B:
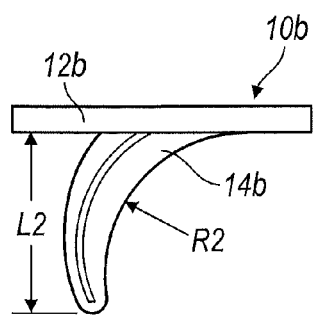
Figure 2C:
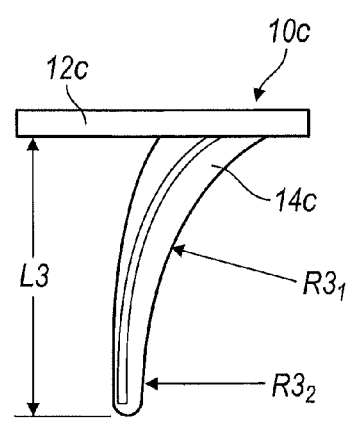

As illustrated in FIGS. 2A-2C, a series of tibial components 10A-10C having tibial trays 12A-12C, may be provided that allow for various lengths (L1-L3) and/or radii (R1-R3$_2$) defined on the respective stems 14A-14C. It is appreciated that the radii of a given stem 14-14C may define a fixed radius along the elongated body (R1 and R2). Alternatively multiple radii may be defined along the stem 14c (R3$_1$ and R3$_2$). In this way, a surgeon may select an appropriate tibial component that provides the desired stem dimensions required for a particular patient.

Figure 3:
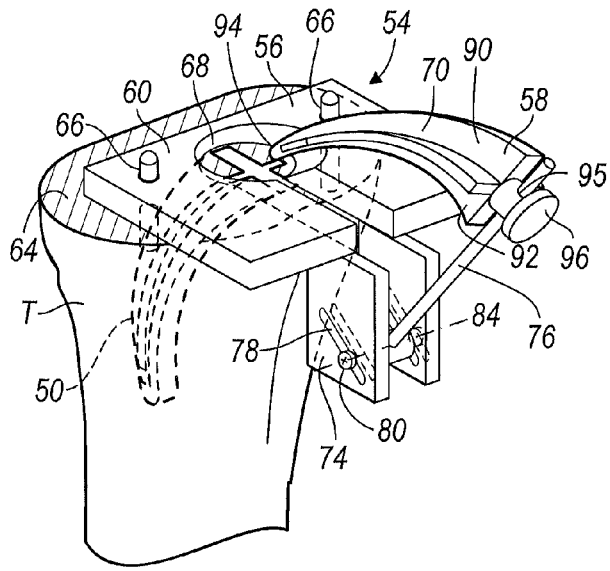
FIG. 3 is a perspective view an exemplary punch operable to create an arcuate canal in the proximal tibia.

Turning now to FIG. 3, preparation of a tibial canal 50 in a tibia T will be described. In one example, a punch assembly 54 having a static portion 56 and a dynamic portion 58 may be used. The static portion 56 of the exemplary punch assembly 54 generally incorporates a platform 60 secured to a proximal tibia 64 by way of fasteners 66. The platform 60 defines a passage 68 for receiving an arcuate punch 70. A flange 74 extends anteriorly from the platform 60 and includes a swing arm 76 rotatably disposed thereon. The swing arm 76 may be translated along a slot 78 defined on the flange 74 to positionally adjust a pivot point 84 of the swing arm 76, to positionally adjust the arcuate path of the platform 60 relative to the tibia T, and to achieve a desired alignment during actuation. A fastener 80 extending through the slot 78 and a bore (not specifically shown) formed in the swing arm 76 may be tightened to preclude translation along the slot 78 once a suitable location has been verified. The fastener 80 defines the pivot 84.

The dynamic portion 58 of the exemplary punch assembly 54 generally includes the swing arm 76 and the punch 70. The punch 70 defines an arcuate punch body 90 substantially conforming to the arcuate tibial 14 stem. The arcuate punch body 90 generally defines an arcuate member tapering from a proximal end 92 to a distal end 94. The punch body 90 may incorporate a planar medial and lateral surface having complementary medial and lateral fins. The swing arm 76 is adapted to be slidably received in a bore 95 formed in the proximal end 92 of the punch body 90. As such, the swing arm 76 is positionally adjustable along the axis of the swing arm 76 to enable positional adjustment of the arcuate path of the punch body 90. Once a desired location is achieved along the swing arm 76, a screw 96 may be tightened to secure the proximal end 92 of the punch body 90 to the swing arm 76.

During operation, the dynamic portion 58 of the punch assembly 54 may be translated about the pivot 84 to drive the distal end 94 of the punch body 90 into the proximal tibia 64. The process is repeated until a suitable canal 50 is prepared. The punch assembly 54 may then be removed from the tibia T. It is appreciated that other punch assemblies or apparatus may be used to form the arcuate canal 50 in the tibia T. In addition, while not specifically shown, the punch body may define a smooth conical arcuate section rather than incorporating the planar surfaces and fins. Furthermore, a series of arcuate punch bodies may be provided having various lengths and radii. As a result, a particular punch body may be selectively secured to the swing arm 76 as needed.

Figure 4:
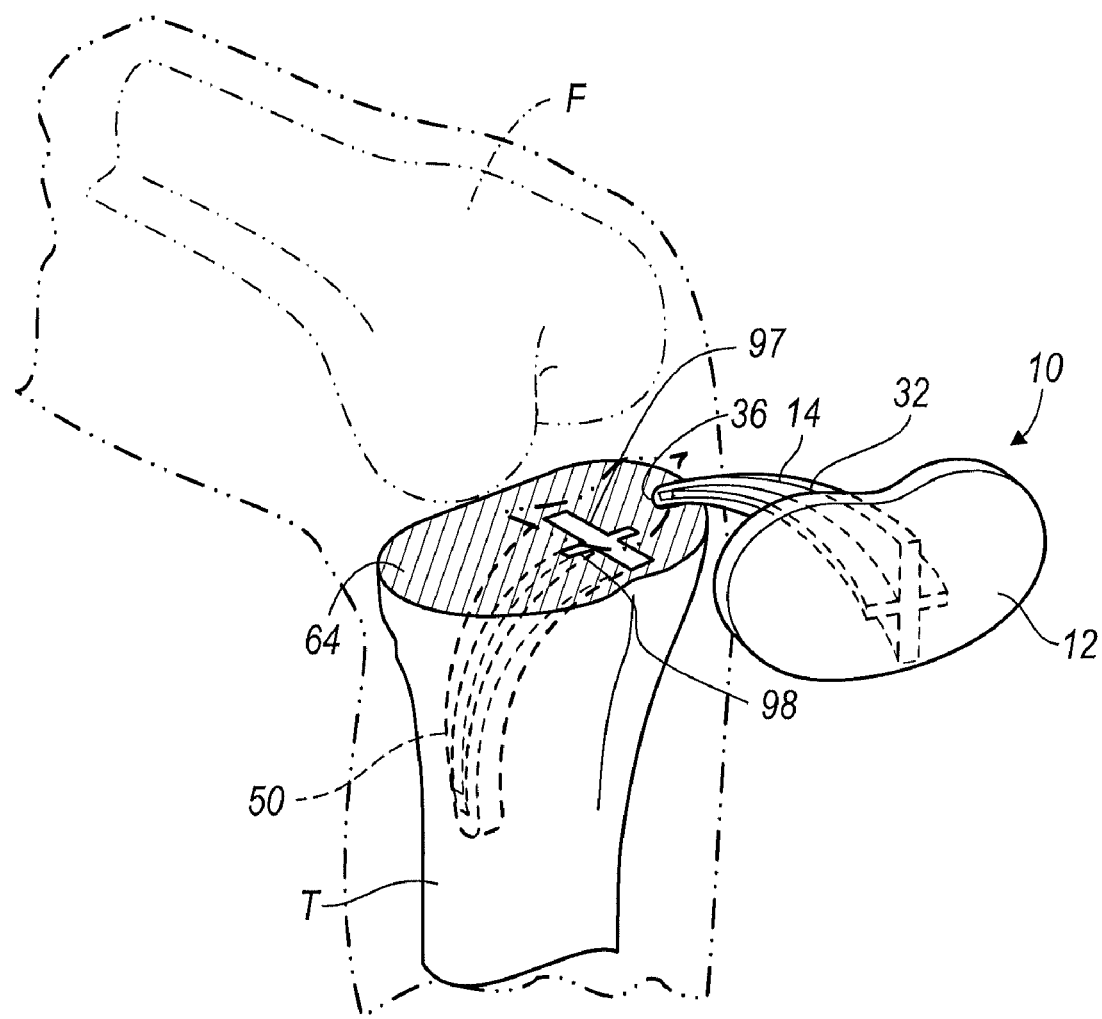
FIG. 4 is a perspective view of the tibial tray of FIG. 1 being implanted into the arcuate canal of the proximal tibia shown with the femur of the natural knee shown in phantom.

Turning now to FIG. 4, the tibial canal 50 formed by the punch assembly 54 is shown. The tibial canal 50 generally defines an anterior/posterior opening 97 and medial/lateral opening 98. Again, the tibial canal 50 may define other arcuate geometries such as, but not limited to, a tapered conical canal suitable to accept the arcuate tibial stem 14.

Figure 5:
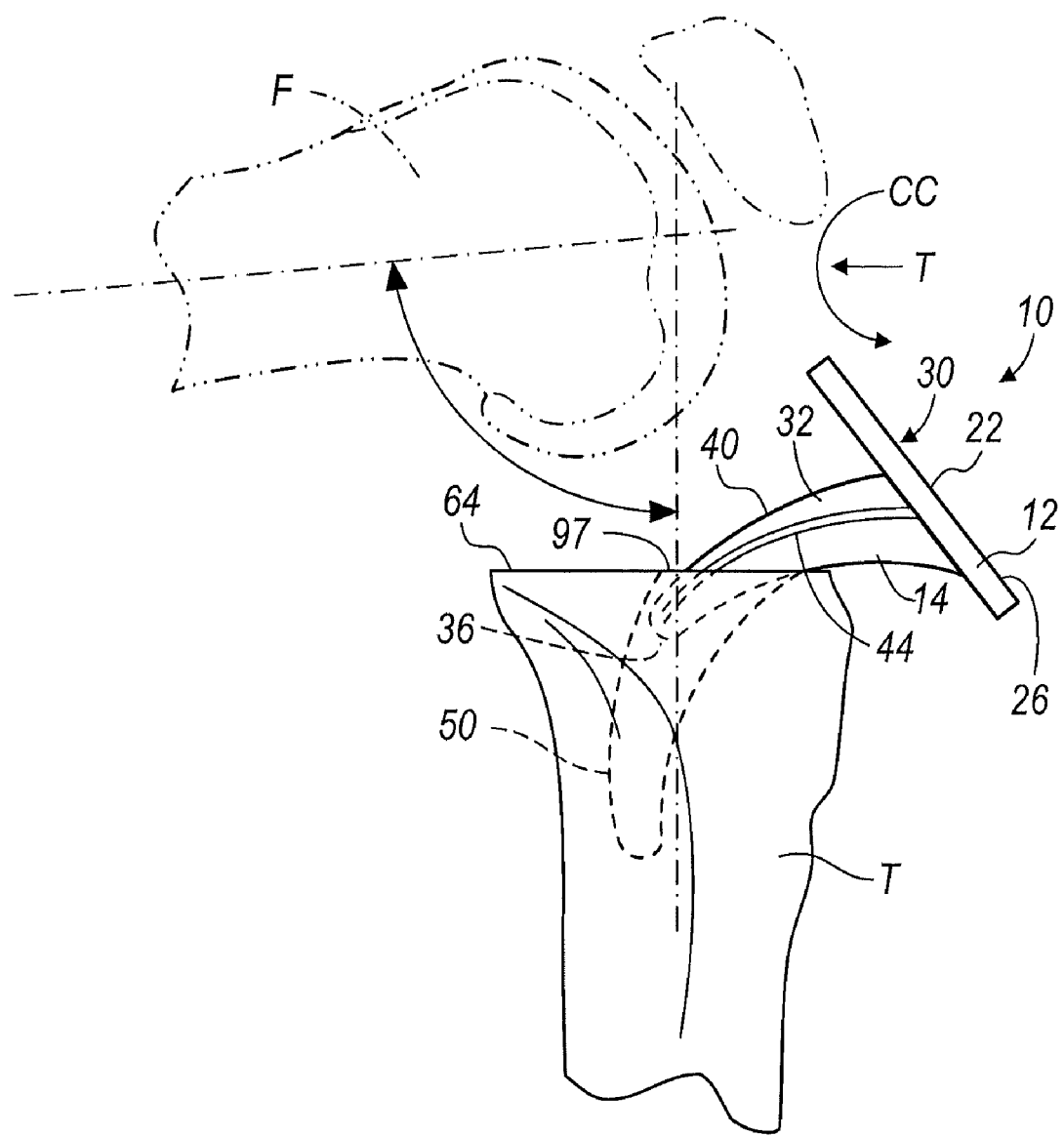
FIG. 5 is a sagittal elevational view the tibial tray of FIG. 1 being implanted into the arcuate canal of the proximal tibia shown with a femur of the natural knee shown in phantom.

With particular reference now to FIGS. 4-6B, implantation of the tibial component 10 will be described. At the outset, the distal tip 36 of the tibial stem 14 is located proximate to the opening of the tibial canal 50 (FIG. 4). The elongated body 32 of the tibial stem 14 is then positioned to substantially align with the anterior/posterior opening 97. Concurrently, alignment of the fins 44, 46 with the medial/lateral opening 98 is verified. Next, the tibial component 10 is rotated in a counterclockwise direction as viewed from FIG. 5 and moved in the posterior direction. Counterclockwise rotation C and posterior translation T of the tibial component 10 causes the tibial stem 14 to be received into the tibial canal 50 in a secure position (FIG. 6A). As illustrated in FIG. 5, the tibial component 10 follows a minimally invasive path during implantation whereby a posterior end of the tibial tray 12 rotates in a path unobstructed by the distal femur F. In addition, the need to manipulate surrounding tissue is minimized during implantation. Bone cement may optionally be used as needed.

Figure 6A:
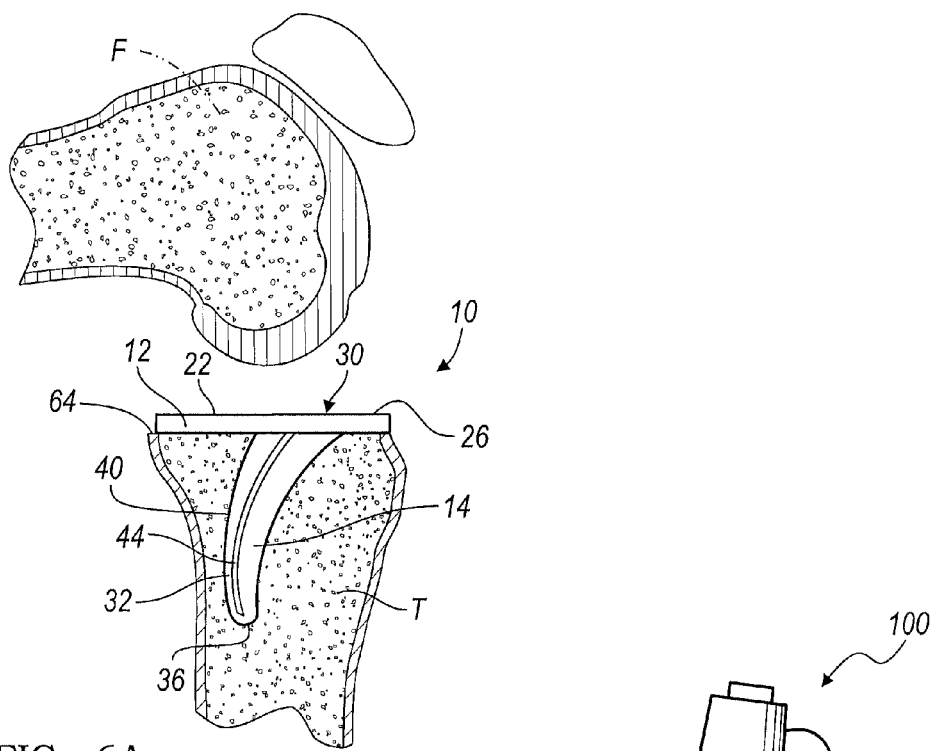
FIG. 6A is a sagittal elevational view of the tibial tray of FIG. 3 shown implanted into the proximal tibia.
Figure 6B:
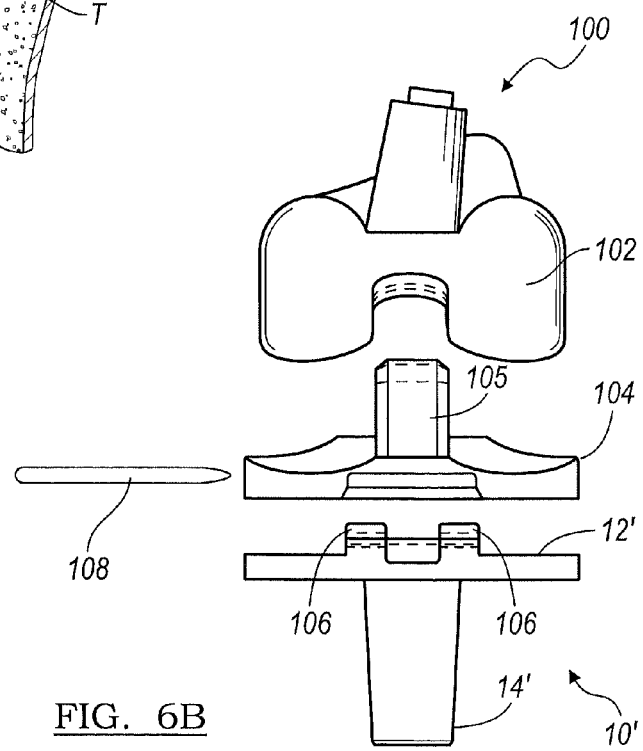
FIG. 6B is an exploded posterior elevational view of a knee joint prosthesis according to the present teachings.

With specific reference to FIG. 6B, the tibial component 10 is shown with a knee joint prosthesis 100. The knee joint prosthesis 100 includes a femoral component 102 adapted to be secured to a surgically resected femur. A tibial insert 104 includes a stabilizing post 105 which projects superiorly from the tibial insert 104. The tibial tray 12' includes an arcuate stem 14'. The tibial tray further includes a pair of integrally formed posts 106 which extend superiorly at the anterior edge of the tibial tray 12'. The posts 106 may cooperate with a locking bar 108 to secure the tibial insert to the tibial tray 12'. It is appreciated that other retaining features may be employed for securing the tibial insert 104 to the tibial tray 12'. Likewise, as mentioned above, the tibial tray may alternatively be adapted for use with a floating tibial insert.

Figure 7:
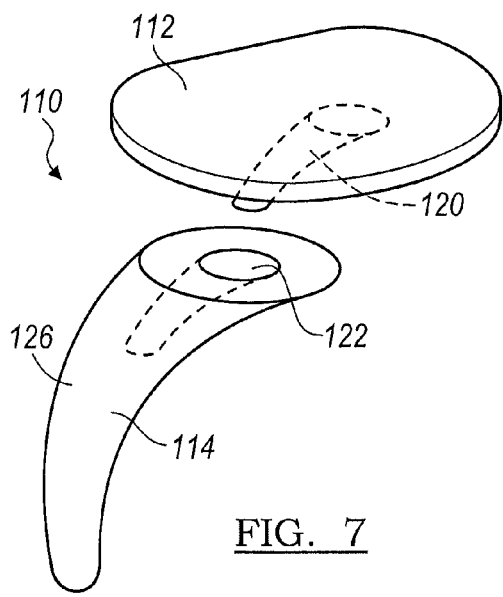
FIG. 7 is a perspective view of a tibial tray and arcuate stem according to another embodiment.
Figure 8A:
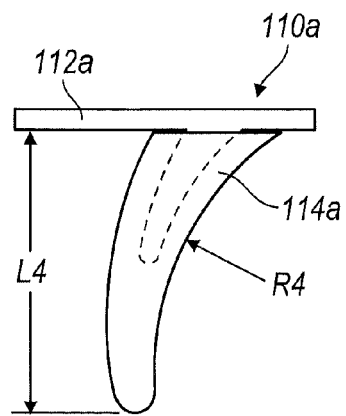
FIG. 8A-8C are sectional views of a series of tibial trays having arcuate stems with various lengths and curvatures according to the embodiment of FIG. 7.
Figure 8B:
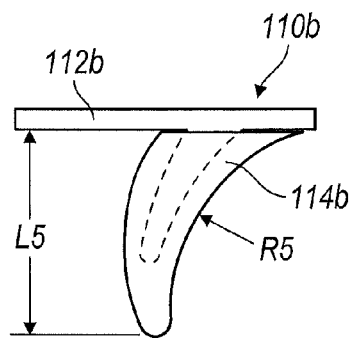
Figure 9:
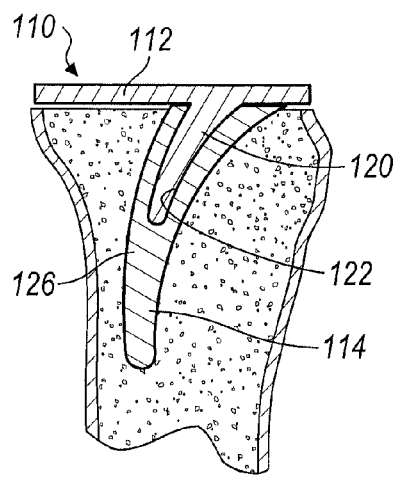
FIG. 9 is a sagittal elevational view of the tibial tray of FIG. 7 shown implanted into the proximal tibia.
Figure 8C:
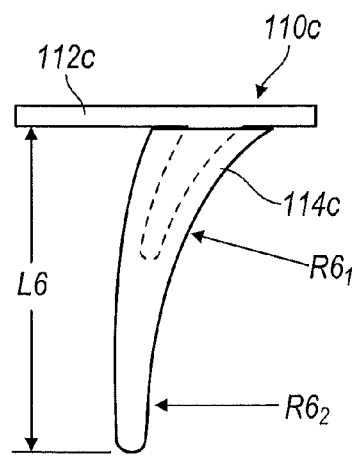

Turning now to FIGS. 7-9, a tibial component 110 according to another embodiment is shown. The tibial component 110 includes a two-piece assembly having a substantially planar platform-like tray 112 having a selectively attachable, inferiorly extending tibial stem 114. A series of tibial components 110A-110C having tibial trays 112A-112C including arcuate stems 114A-114C may be provided. The arcuate stems 114A-114B may have various radii (R4 and R5) and/or lengths (L4-L6) and may be employed according to patient needs. Likewise, the stem 114C may define multiple radii $R6_1$ and $R6_2$ (FIG. 8C).

In one example, the tray 112 defines an inferiorly extending male portion 120 adapted for receipt into a corresponding female opening 122 defined on the tibial stem 114 (FIG. 7). The male portion 120 generally defines an arcuate body 126 extending in the posterior/inferior direction. In one example, the respective male portion and female opening 120 and 122 may be securely attached by friction fit. Additionally or alternatively, biocompatible adhesive may be employed at the interface between the male portion 120 and female opening 122. It is appreciated that the male portion may be alternatively formed on the stem 114 and the female portion alternatively formed on the tray 112.

While the tibial stem 114 is illustrated as having a generally conical outer surface, it is appreciated that the tibial stem 114 may alternatively incorporate a planar medial and lateral surface such as associated with the tibial stem 14. Additionally, perpendicular fins may be incorporated on the tibial stem 114.

Figure 10:
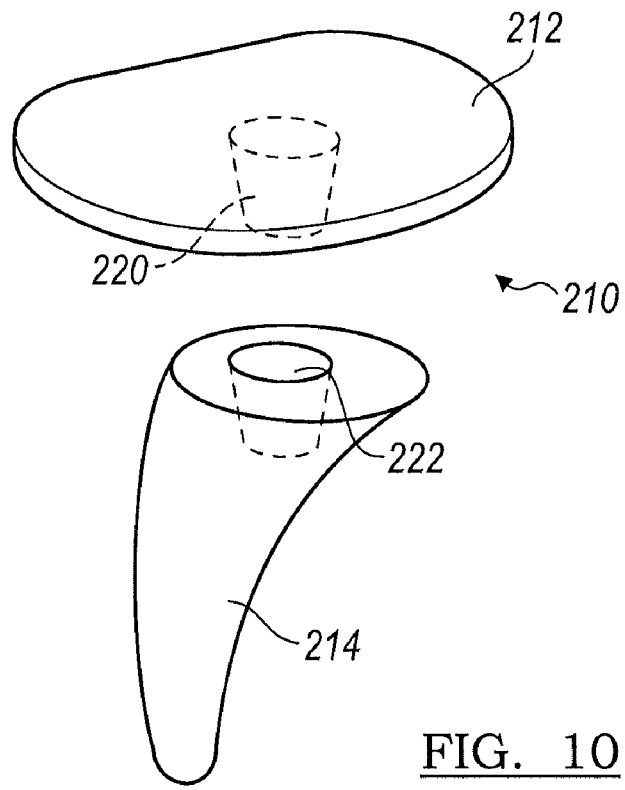
FIG. 10 is a perspective view of a tibial tray and arcuate stem according to another embodiment.
Figure 11:
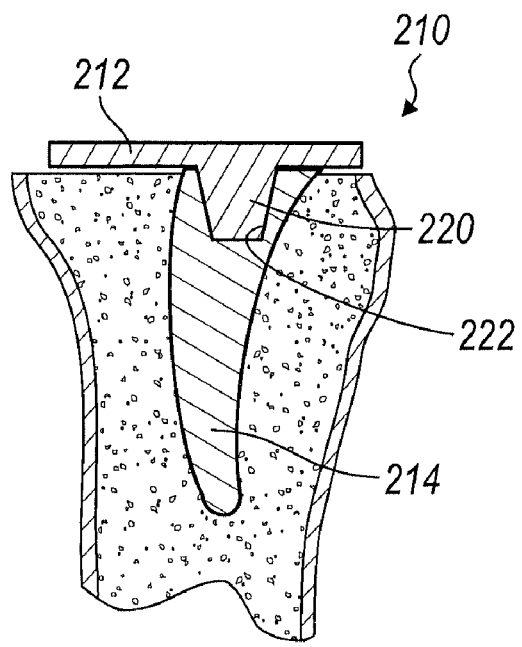
FIG. 11 is a sagittal elevational view of the tibial tray of FIG. 10 shown implanted into the proximal tibia.

With reference now to FIGS. 10 and 11, a tibial component 210 according to another embodiment is shown. The tibial component 210 includes a two-piece assembly having a substantially planar platform-like tray 212 having a selectively attachable, inferiorly extending tibial stem 214. The tibial component 210 is modular such that various arcuate stems having various radius and/or lengths may be employed according to patient needs. The tibial component 210 defines an inferiorly extending male portion 220 adapted for receipt into a corresponding female opening 222 defined on the stem 214. It is appreciated that the male portion may be alternatively formed on the stem 214 and the female portion alternatively formed on the tray 212.

As illustrated in FIG. 11, the male portion 220 extends generally perpendicularly from the tray 212. A series of stems may be provided having a corresponding female opening. In one example, the respective male portion and female opening may be securely attached by friction fit. Additionally or alternatively, biocompatible adhesive may be employed at the interface between the male portion 220 and the female opening 222. It is appreciated that the two-piece assembly may be adapted for use with a knee joint replacement as described in relation to FIG. 6B.

Figure 12:
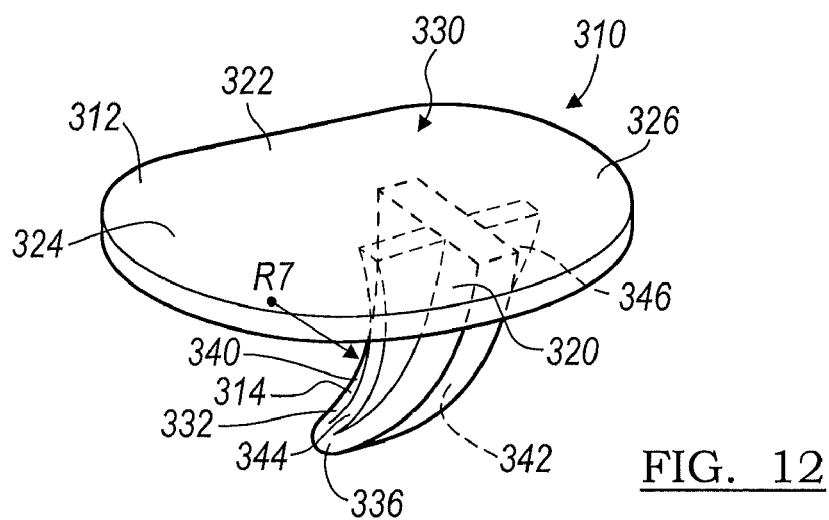
FIG. 12 is a perspective view of a tibial tray and arcuate stem according to another embodiment.
Figure 13:
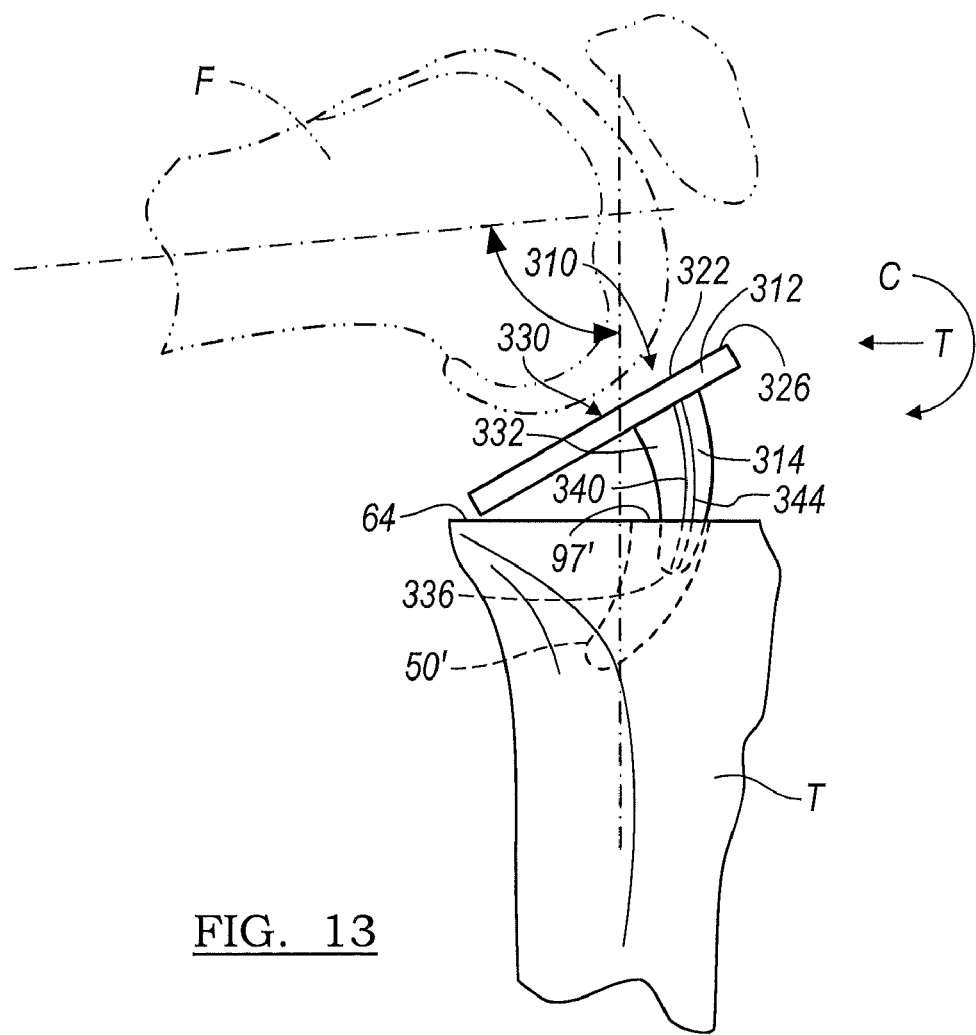
FIG. 13 is a perspective view of the tibial tray of FIG. 12 being implanted into an arcuate canal of the proximal tibia shown with the femur of the natural knee shown in phantom.

With reference now to FIGS. 12 and 13, a tibial component 310 according to another embodiment is shown. The tibial component 310 includes a substantially planar platform-like tray 312 having a fixed, inferiorly extending tibial stem 314. For simplicity, the tibial component 310 is identified with like reference numerals as associated with the tibial component 10 shown in FIG. 1 and increased by 300.

The tibial stem 314 defines an elongated body 332 having an arcuate contour. The tibial stem 314 extends from a portion of the tibial tray 312 to the distal tip 336 in a generally posterior/inferior direction defining a radius R7. As shown in FIG. 13, the tibial stem 314 extends in a generally clockwise direction (posteriorly) in an inferior direction from the tibial tray 312. In contrast, the tibial stem 14 shown in FIG. 1 extends in a generally counterclockwise direction (anteriorly) in an inferior direction from the tibial tray 12.

With continued reference to FIG. 12 and further reference to FIG. 13, implantation of the tibial component 310 will be described. It is appreciated, that preparation of a tibial canal 50' may be accomplished by methods disclosed herein while utilizing a punch assembly having a complementary structure. At the outset, the distal tip 336 of the tibial stem 314 is located proximate to the opening of the tibial canal 50'. The elongated body 32 of the tibial stem 14 is then positioned to substantially align with the anterior/posterior opening 97'. An angle may be defined between the tibial plateau and the tibial tray 312. In one example the angle may be between 20 and 40 degrees such as 30 degrees. It is appreciated that other angles may be defined between the tibial plateau and the tibial tray 312 during implantation.

Concurrently, alignment of the fins 344, 346 with the medial/lateral opening (not specifically shown) is verified. Next, the tibial component 310 is rotated in a clockwise direction. As illustrated in FIG. 13, the tibial component 310 follows a minimally invasive path during implantation whereby the tibial tray 312 is initially located and subsequently rotated in a path unobstructed by the distal femur F. In addition, the need to manipulate surrounding tissue is minimized during implantation. Bone cement may optionally be used as needed.

It is appreciated that the tibial component 310 may be provided as a series of tibial stems having various lengths and radii such as described above with respect to the tibial component 10. Likewise, the tibial component 310 may comprise a two-piece assembly such as described herein with respect to the tibial components 110 and 210. Furthermore, the tibial component may comprise a knee joint prosthesis such as illustrated in FIG. 6B.

Figure 14:
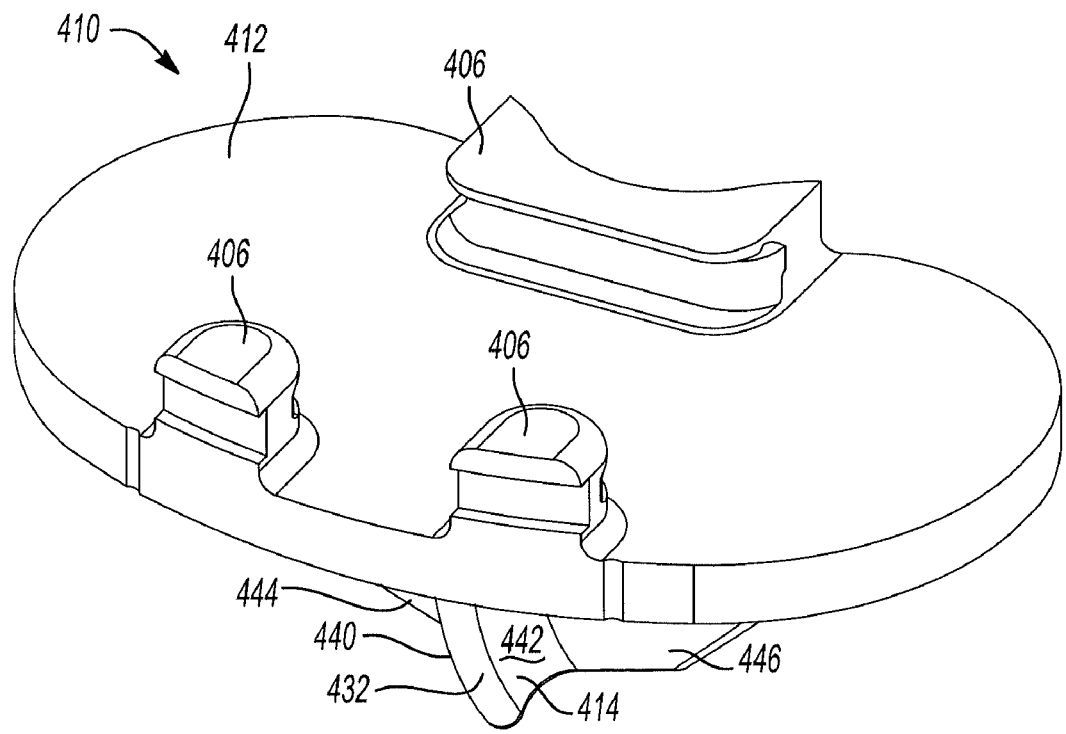
FIG. 14 is a perspective view of a tibial tray and arcuate stem according to another embodiment.
Figure 15:
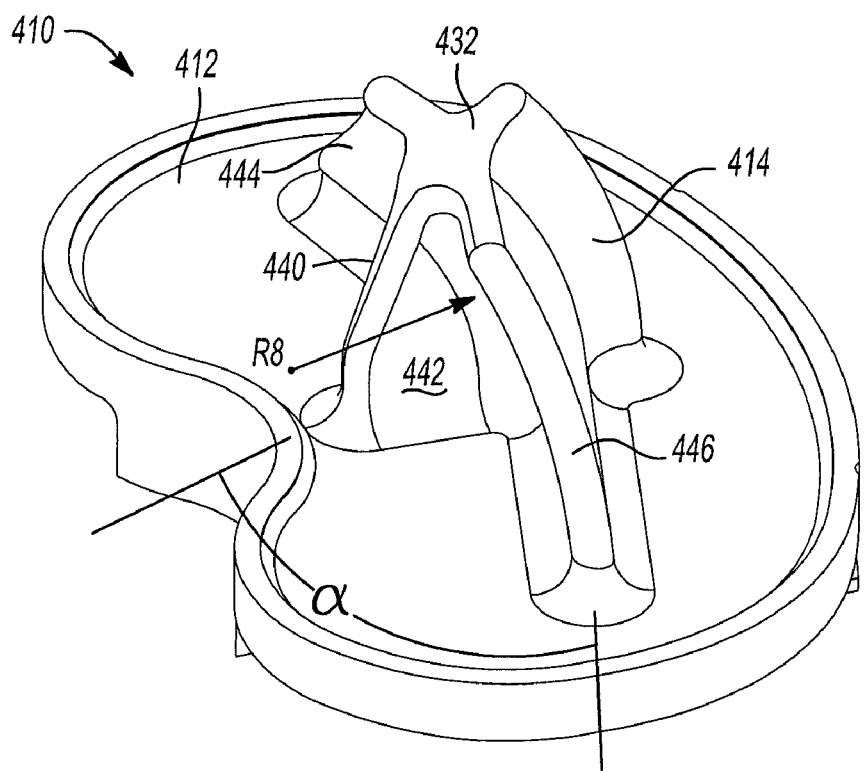
FIG. 15 is an inferior perspective view of the tibial tray and arcuate stem of FIG. 14.

With reference now to FIGS. 14 and 15, a tibial component 410 according to another embodiment is shown. The tibial component 410 includes a substantially planar platform-like tray 412 having a fixed, inferiorly extending tibial stem 414. For simplicity, the tibial component 410 is identified with like reference numerals as associated with the tibial component 10 shown in FIG. 1 and increased by 400.

The tray 412 includes a plurality of integrally formed posts 406 extending superiorly at the anterior and posterior edge of the tibial tray 412. The posts 406 can couple to a tibial insert or bearing 104 of the type shown in FIG. 6B and described above. A locking bar 108 of the type shown in FIG. 6B and described above can be used to secure the tibial insert 104 to the posts 406. It is appreciated that other retaining features may be employed for securing the tibial insert 104 to the tibial tray 412.

Likewise, the tibial tray 412 may be adapted for use with any suitable type of knee joint prosthesis, including, for example, a hinged knee joint prosthesis, a knee joint prosthesis with a fixed bearing, a knee joint prosthesis with a floating bearing, a knee joint prosthesis with a rotating bearing, a fully constrained knee joint prosthesis, a posterior stabilized knee joint prosthesis, and a cruciate retaining (C.R.) knee joint prosthesis.

The tibial stem 414 defines an elongated body 432 having a generally arcuate contour defining a radius R8. It will be appreciated that the radius R8 could be of any suitable value, and it will be appreciated that the tibial stem 414 could include a plurality of radii. It will also be appreciated that the stem 414 can be integrally coupled to the tray 412, or the stem 414 can be removably coupled to the tray 412 similar to the embodiments described above. Moreover, it will be appreciated that the tibial component 410 can be modular, similar to the embodiments described above such that various arcuate stems 414 having various radii and/or lengths may be coupled to the tray 412 and employed in the knee joint prosthesis.

The elongated body 432 defines a planar medial surface 440 and a planar lateral surface 442. A medial and lateral fin 444, 446 are arranged along the respective medial and lateral surfaces 440, 442. The medial and lateral fins 444, 446 may discourage rotation of the tibial component 410 about the axis of the stem 414 once implanted. In some embodiments, the medial and lateral fins 444, 446 are each planar and disposed at a positive acute angle, $\alpha$, with respect to a posterior end of the medial and lateral surfaces 440, 442 (FIG. 15).

In some embodiments, when the tibial stem 414 is implanted in the tibia bone, the tibial stem 414 extends from a portion of the tibial tray 412 to the distal tip 436 in a generally posterior and inferior direction similar to the embodiment described above in relation to FIGS. 12 and 13. However, it will be appreciated that the tibial stem 414 can extend in any suitable direction, including a generally anterior and inferior direction from the tibial tray 412.

With reference now to FIGS. 16-21, another embodiment of a punch assembly 554 is illustrated. The punch assembly 554 can be used to prepare and form a tibial canal 50" (i.e., an aperture in the tibia T) for securement of the tibial component 410, as will be described in greater detail below. For simplicity, the punch assembly 554 is identified with like reference numerals as associated with the punch assembly 54 shown in FIG. 3 and increased by 500.

The punch assembly 554 can be configured for a right or left leg. Also, in some embodiments, the punch assembly 554 can be universal such that the same punch assembly 554 can be used in association with both right and left legs.

The punch assembly 554 includes a static or base component 556 and a dynamic or boring component 558. Operation of the punch assembly 554 is similar to the punch assembly 54 shown in FIG. 3 because the dynamic component 558 is supported for movement relative to the static component 556 along a generally arcuate path P to prepare and form the arcuate tibial canal 50" (FIG. 16), as will be explained in greater detail below.

In some embodiments, the static component 556 and the dynamic component 558 are each made out of stainless steel. However, it will be appreciated that the static and dynamic components 556, 558 can be made out of any suitable biological compatible material.

Figure 16:
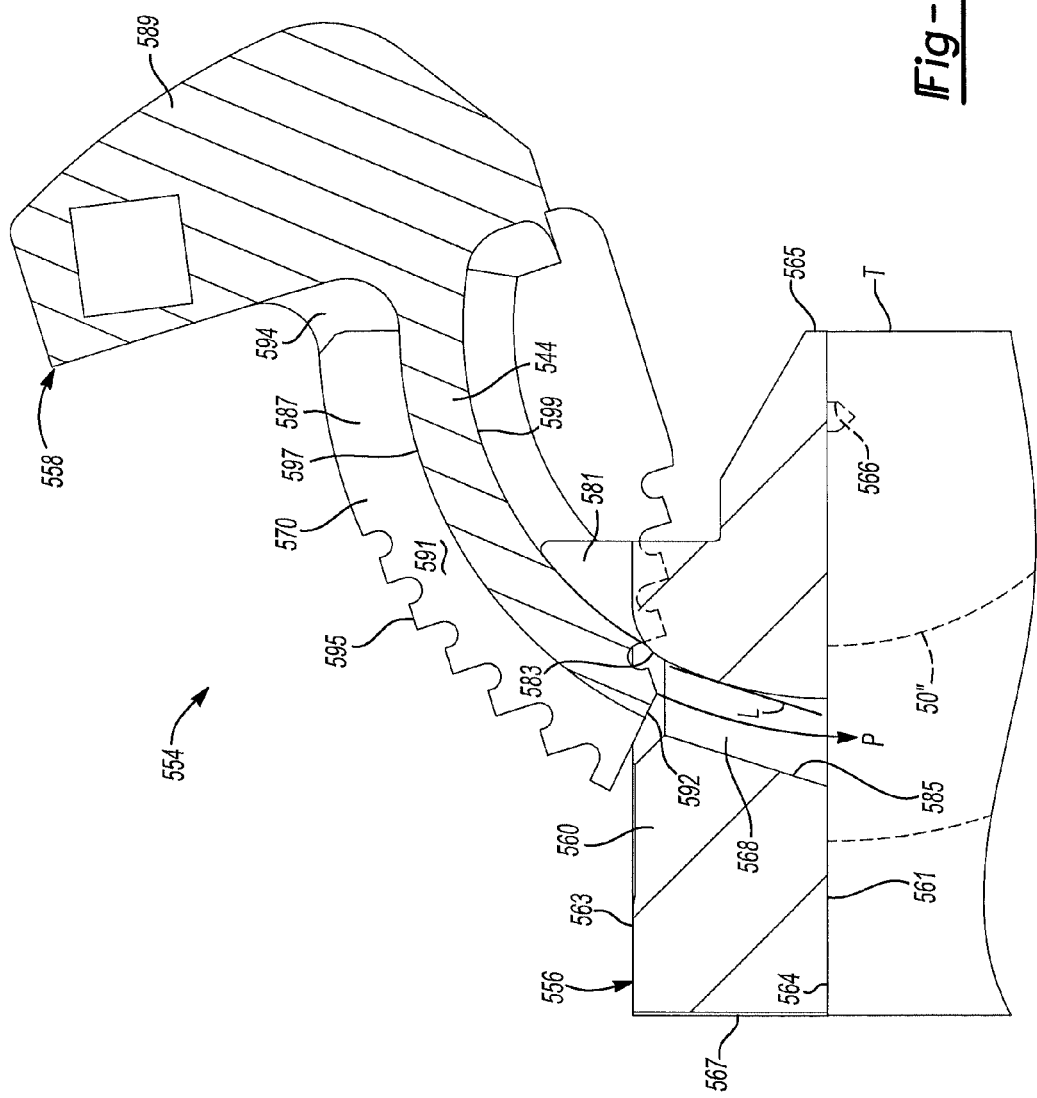
FIG. 16 is a sectional view of a punch assembly according to another embodiment.
Figure 17:
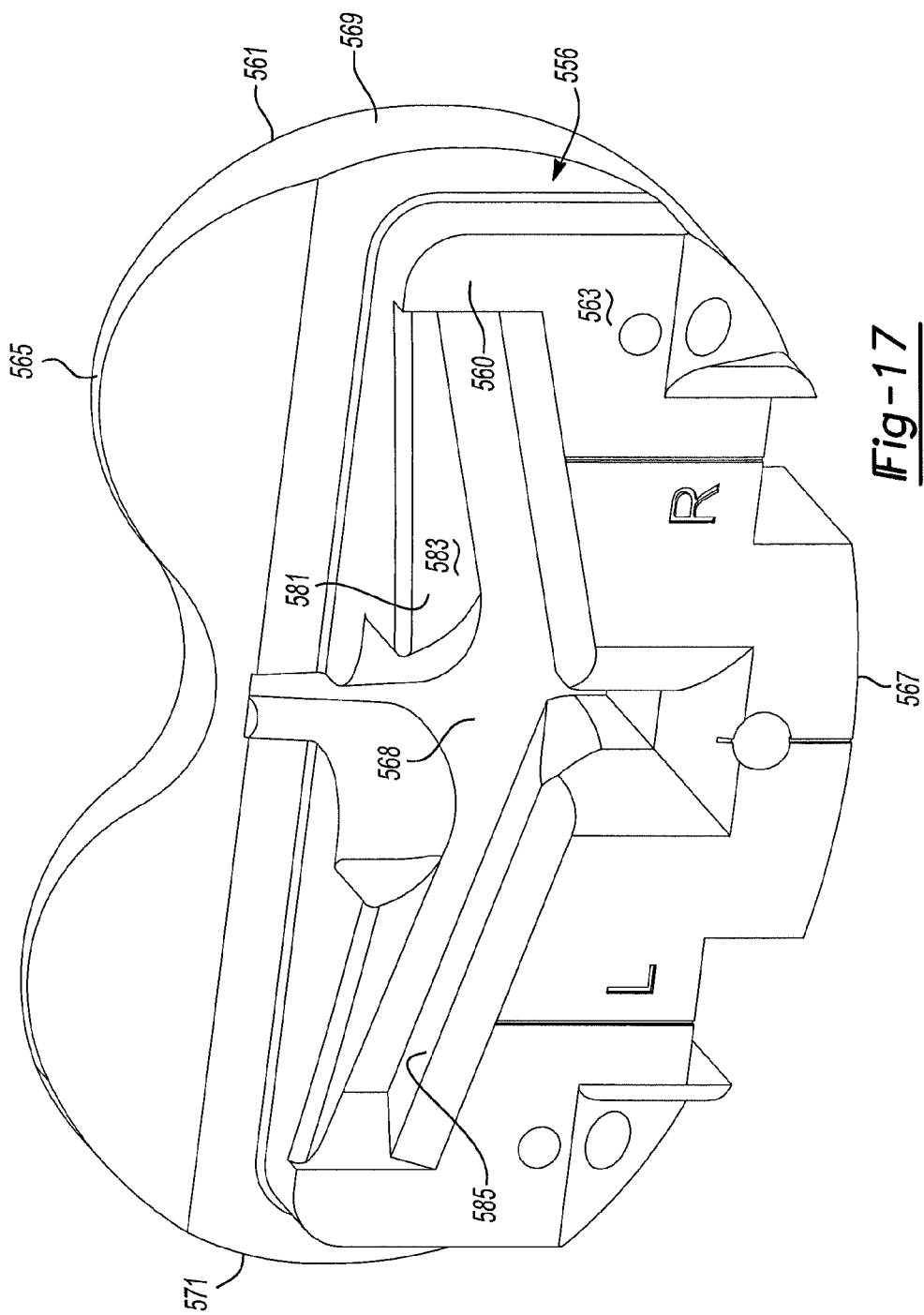
FIG. 17 is a superior perspective view of a static component of the punch assembly of FIG. 16.
Figure 18:
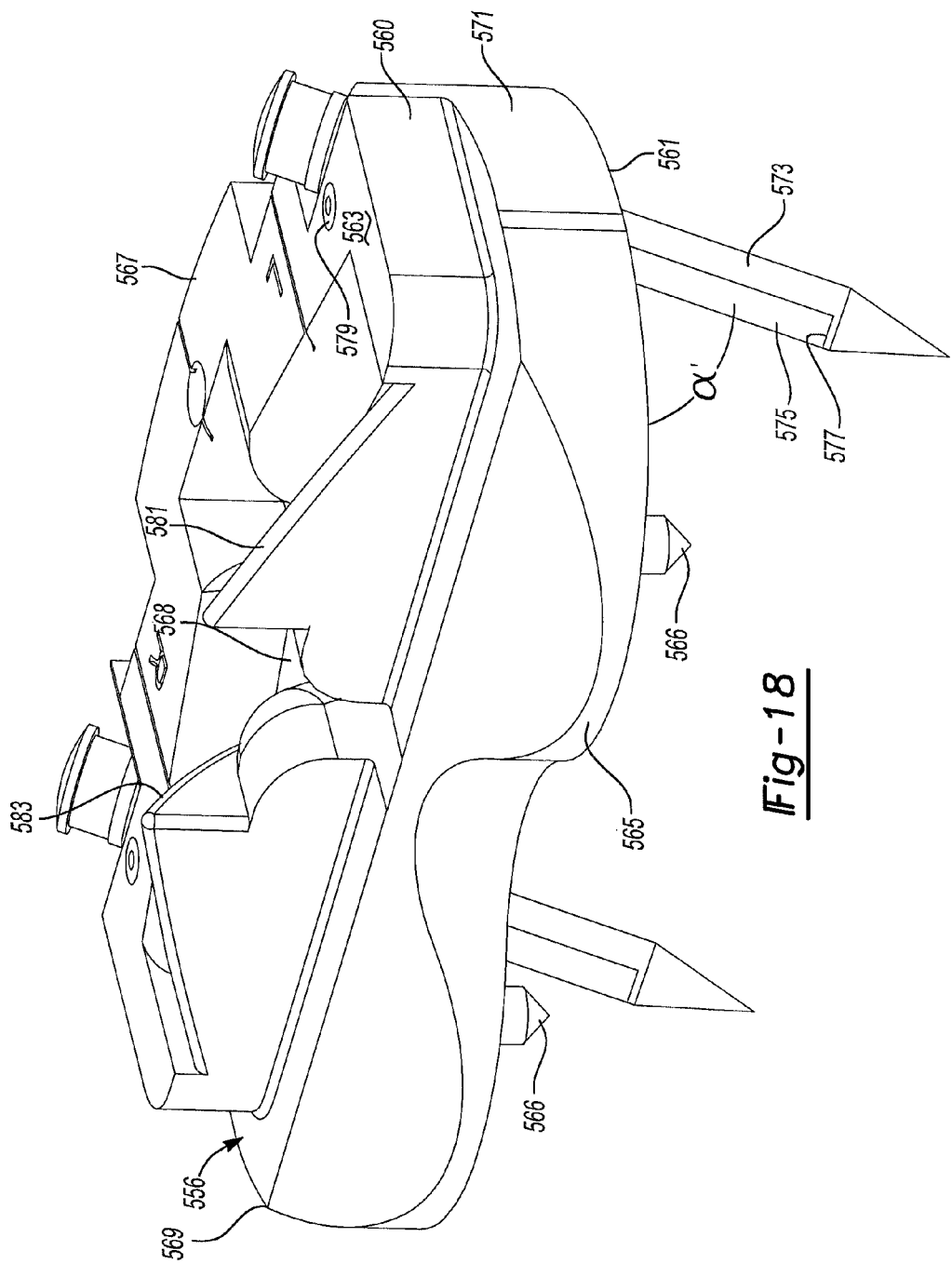
FIG. 18 is a posterior perspective view of the static component of the punch assembly of FIG. 16.
Figure 19:
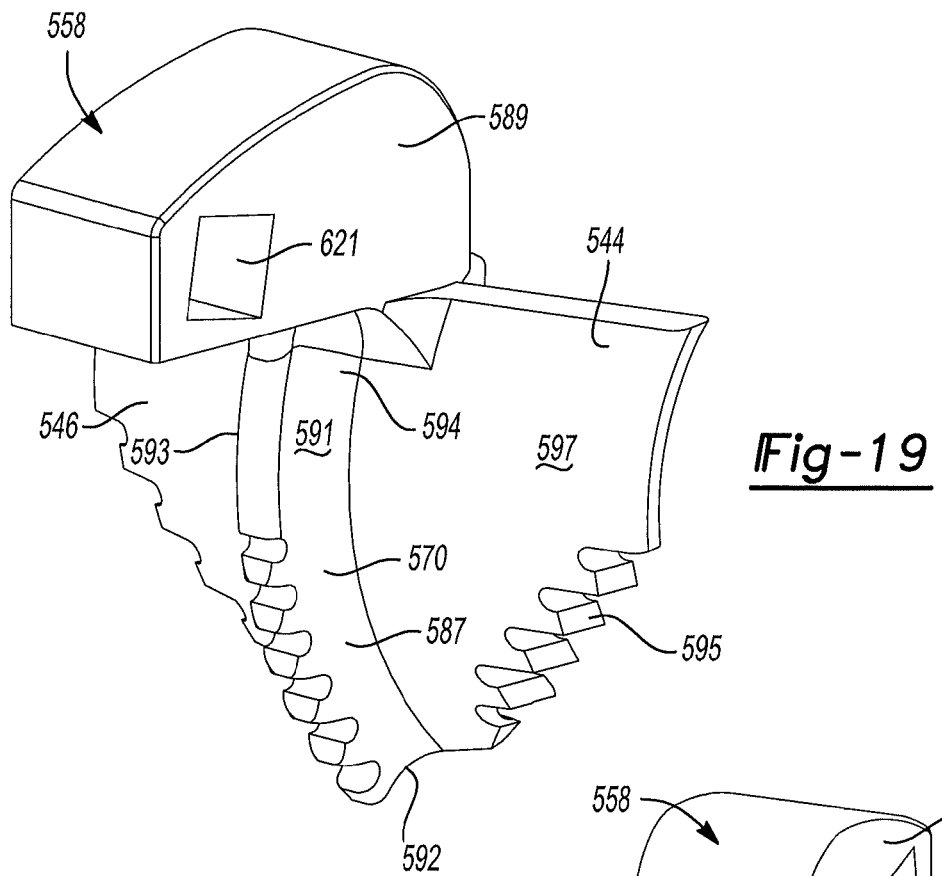
FIG. 19 is an anterior perspective view of a dynamic component of the punch assembly of FIG. 16.
Figure 20:
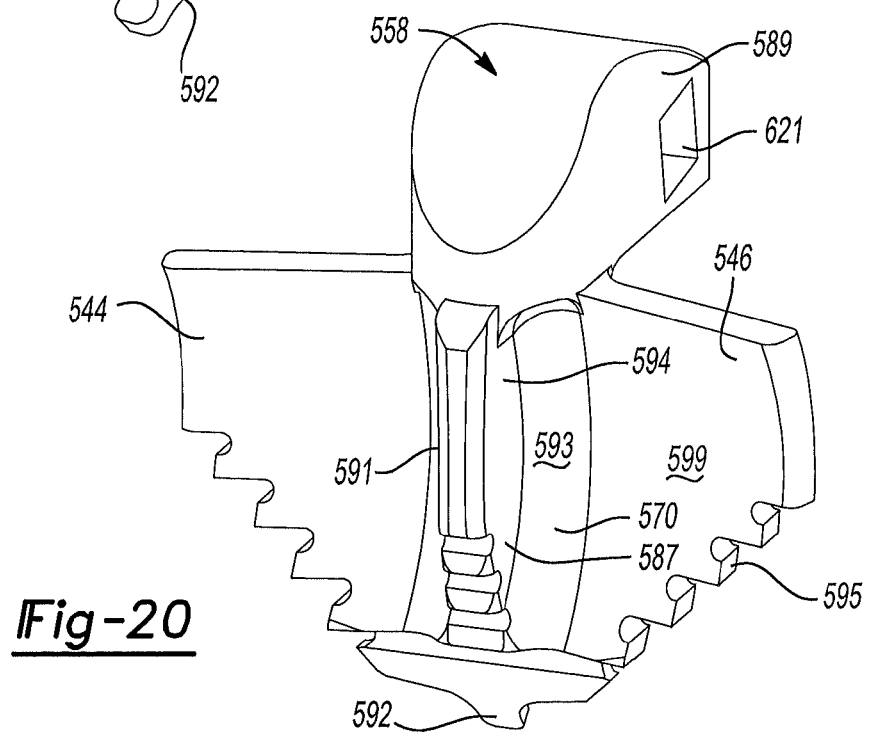
FIG. 20 is a posterior perspective view of the dynamic component of the punch assembly of FIG. 16.

As illustrated in FIGS. 16-18 and 21, the static component 556 includes a platform 560 with a bone engaging surface 561 and a superior surface 563. The platform 560 includes a posterior side 565 and an anterior side 567. The platform 560 also includes a first transverse side 569 and a second transverse side 571 (FIGS. 17 and 18).

The platform 560 is configured to be supported by and coupled to a proximal, resected tibia 564 by way of first fasteners 566 and second fasteners 573 (FIG. 18). The first fasteners 566 are integrally coupled to the platform 560 adjacent the posterior side 565, and the first fasteners 566 extend from the bone engaging surface 561 to enter the tibia proximal tibia 564. The second fasteners 573 are adjustably coupled to the platform 560 adjacent the anterior side 567. More specifically, the second fasteners 573 extend through corresponding apertures in the platform 560 at a positive acute angle, $\alpha'$, relative to the bone engaging surface 561 (FIG. 18). In other words, the second fasteners 573 extend from the superior surface 563 to the bone engaging surface 561 at the angle, $\alpha'$, in a generally posterior, inferior direction. The second fasteners 573 can slide axially through corresponding apertures in the platform 560.

To attach the platform 560 to the proximal tibia 564, the first fasteners 566 are driven into the tibia T, and then the second fasteners 573 are driven into the tibia T. The angular orientation of the second fasteners 573 allows for more convenient securement of the platform 560 because the second fasteners 573 extend out and can be driven into the tibia T from an anterior position, and a less severe flexion angle is necessary between the femur (not specifically shown) and the tibia T is necessary to provide clearance. Also, the angular orientation of the second fasteners 573 allow for improved securement of the platform 560 because the second fasteners 573 have improved leverage against the forces induced by the dynamic portion 558 as the dynamic portion 558 is driven into the tibia T, as will be described in greater detail below.

Also, in some embodiments, the second fasteners 573 each include a generally planar surface 575 extending longitudinally thereon and a corresponding collar 577 on an inferior end (see FIG. 17). A set screw 579 extends partially through the platform 560 adjacent a corresponding second fastener 573. The set screw 579 interferes with the collar 577 of the corresponding second fastener 573 to limit movement of the corresponding second fastener 573 out of the platform 560. As such, the second fasteners 573 are unlikely to be inadvertently removed from the platform 560 for added convenience.

As most clearly shown in FIGS. 16 and 17, the platform 560 defines a passage 568 for receiving the dynamic component 558, as will be discussed in greater detail below. The passage 568 extends through the platform 560 from the superior surface 563 to the bone engaging surface 561. Also, in some embodiments, the passage 568 is generally cruciform in shape.

The platform 560 also includes a plurality of ramps 581 extending from the superior surface 563. The ramps 581 are disposed adjacent the passage 568 and adjacent the posterior side 565. Also, the ramps 581 each include a first support surface 583 that extends from a superior end of the respective ramp 581 and through the passage 568 so as to partially define the passage 568. In some embodiments, the first support surface 583 is generally arcuate in shape so as to define the arcuate path P of the dynamic component 558 as will be described.

In addition, the platform 560 includes a third surface 585 (see FIG. 16) that cooperates with the first support surface 583 to partially define the passage 568. As shown in FIG. 16, the third surface 585 generally faces the first support surface 583. Also, in some embodiments, the third surface 585 is planar and is parallel and disposed at a distance from an imaginary line L that is substantially tangent to the first support surface 583.

As shown in FIGS. 16 and 19-21, the dynamic portion 558 of the exemplary punch assembly 554 includes a punch 570 and a bulbous head 589. The punch 570 includes a stem 587. In some embodiments, the stem 587 substantially conforms in shape to the arcuate tibial stem 414, shown in FIGS. 14 and 15. The stem 587 has an arcuate contour and tapers from a proximal end 592 to a distal end 594. Also, the stem 587 can include any suitable radius, and in some embodiments, the stem 587 defines a plurality of radii.

The stem 587 may incorporate a first side surface 591 and a second side surface 593. The stem 587 can also include a first fin 544 extending transversely from the first side surface 591 and a second fin 546 extending transversely from the second side surface 593. Furthermore, the stem 587 can include a plurality of teeth 595. It will be appreciated, however, that the stem 587 can be have a smooth, conical, arcuate section rather than incorporating the planar side surfaces 591, 593 and the fins 544, 546.

The stem 587 is configured to pass through the passage 568 and slide on the support surface 583 of the ramps 581. Thus, in some embodiments, the stem 587 closely conforms in shape to the passage 568. Specifically, in some embodiments, the stem 587 has a cruciform shape that conforms to that of the passage 568. More specifically, the fins 544, 546 include an anterior surface 597 and a posterior surface 599. The posterior surface 599 defines a support surface having an arcuate contour that conforms in shape to the arcuate contour of the support surface 583 of the ramps 581 of the static component 556. As such, the posterior surface 599 is supported by and slides on the support surface 583 of the ramps 581 along the arcuate path P to prepare an aperture in the tibia bone T (FIGS. 16 and 21). Also, as the stem 587 moves through the passage, the anterior surface 597 of the fins 544, 546 is supported by the third surface 585 of the static component 556 to maintain sliding engagement of the posterior surface 599 of the stem 587 and the support surface 583 of the ramps 581. Accordingly, first support surface 583 and the third support surface 585 cooperate with the posterior surface 599 and the anterior surface 597, respectively, to guide the movement of the stem 587 relative to the static component 556. In other words, the stem 587 is guided along a single, directed arcuate path P while moving through the passage 568 because the stem 587 closely corresponds in shape to that of the passage 568.

The punch assembly 554 also includes a first handle 601 and a second handle 603, as shown in FIG. 21. The first handle 601 includes a grip portion 605 and a coupling portion 607. The coupling portion 607 removably couples to the static component 556. In some embodiments, the coupling portion 607 includes a post 611 and a plurality of retractable bearings 609 movably coupled to the post 611. The bearings 609 are biased outward from the post 611, and the coupling portion 607 includes a button 613 that can be actuated to cause the bearings 609 to retract into the post 611. When the bearings 609 are retracted, the post 611 fits into a corresponding attachment hole 615a, 615b extending posteriorly from the anterior side 567 of the static component 556. Then, when the button 613 is released, interference between the bearings 609 and the interior surfaces of the attachment hole 615a, 615b couples the first handle 601 to the static component 556. The first handle 601 is released from the static component 556 by actuating the button 613 and pulling the post 611 from the corresponding attachment hole 615a, 615b.

In some embodiments, the static component 556 includes two attachment holes 615a, 615b, and one attachment hole 615a is used for preparing a tibia T of a right leg, and the other attachment hole 615b is used for preparing a tibia T of a left leg. Also, the static component 556 can include a symbol on the superior surface 563 that indicates whether the attachment hole 615a, 615b is intended for the right or left leg. For instance, in some embodiments, the static component includes the letter "R" above the attachment hole 615a and the letter "L" above the attachment hole 615b. Furthermore, in some embodiments, the attachment holes 615a, 615b are offset relative to a center axis S of the static component 556. In some embodiments, this offset is included according to the teachings of U.S. patent application Ser. No. 10/702,335, filed, Nov. 6, 2003, which is hereby incorporated by reference in its entirety.

Additionally, in some embodiments, the grip portion 605 defines a first axis H, and the coupling portion 607 defines a second axis H'. In some embodiments, the first axis H is offset from the second axis H'. More specifically, in some embodiments, the first axis H and the second axis H' are substantially parallel and disposed at a distance away from each other. In some embodiments, the amount of offset between the first axis H and the second axis H' is approximately equal to the amount of offset between the attachment holes 615a, 615b and the center axis S of the static component 556. As such, when the first handle 601 is coupled to the static component 556, the grip portion 605 can be substantially aligned with the center axis S of the static component 556 for improved leverage, and yet the first handle 601 is less likely to interfere with ligaments and other biological tissue of the patella, etc.

Furthermore, the second handle 603 includes a grip portion 617 and a coupling portion 619. The grip portion 617 is disposed at a positive angle (e.g., a right angle) relative to the grip portion 617. The grip portion 617 includes a plurality of ridges and depressions to conform to the shape of the hand and fingers for improved gripping. The coupling portion 619 includes a plurality of flat sides and conforms in shape to an aperture 621 defined in the head 589 of the dynamic component 558. As will be described in greater detail, the second handle 603 is used to extract the dynamic component 558 from the tibia T after it has been driven into the tibia T. Furthermore, the second handle 603 includes a claw member 623 at one end of the grip portion 617 that can be used to pull out and extract the fasteners 573 of the static component 556 from the tibia T.

Referring now to FIGS. 16 and 21, formation of the tibial canal 50" in the tibia T using the punch assembly 554 will now be discussed. Initially, the static component 556 is located on and coupled to the proximal tibia 564 using the first fasteners 566, and then the second fasteners 573 are driven into the tibia T. The first handle 601 can be coupled to the static component 556 while coupling the static component 556 to the tibia T for added control.

Then, the dynamic component 558 is positioned in a superior position relative to the static component 556 such that the posterior surface 599 of the fins 544, 546 is supported on the support surface 583 of the static component 556. Next, with the first handle 601 coupled to the static component 556, force is transferred to the head 589 of the dynamic portion 558 of the punch assembly 554 using a hammer or other similar tool to slidingly translate the dynamic portion 558 along the arcuate path P and drive the distal end 594 of the punch body 590 into the proximal tibia 564. This is repeated until a suitable canal 50" is prepared. The punch assembly 554 may then be removed from the tibia T using the second handle 603. Then, the claw portion 623 of the second handle 603 can be used to remove the fasteners 573 from the tibia T, and the static component 556 can be pulled from the tibia T using the first handle 601. Subsequently, the tibial component 10, 110, 210, 310, 410 of the knee joint prosthesis can be coupled to the tibia T and the remaining portions of the knee joint prosthesis can be assembled.

In some embodiments, the punch assembly 554 is used to form an arcuate tibial canal 50" that extends toward a generally posterior, inferior direction into the tibia bone T. This orientation can allow the tibial canal 50" to be prepared and the tibial component 410 to be implanted more easily because there is increased clearance between the femur, patella and the punch assembly 554. However, it will be appreciated that the punch assembly 554 can be configured to form a tibial canal 50" in any desired orientation, including a generally anterior, inferior direction into the tibia T.

In some embodiments, the tibia T is sized before using the punch assembly 54, 554 to prepare the tibial canal 50, 50', 50". Sizing of the tibia bone T can be performed in order to select a proper tibial tray 12, 12', 112, 212, 312, 412 and/or a stem 14, 14', 114, 214, 314, 414 for the prosthesis. More specifically, in one embodiment, a "trial" tibial component 10, 10', 110, 210, 310, 410 is used to size the tibia bone T. In some embodiments, the "trial" tibial component 10, 10', 110, 210, 310, 410 includes a modular tibial tray 12, 12', 112, 212, 312, 412 and a modular stem 14, 14', 114, 214, 314, 414 of the types described above in relation to FIGS. 7-9 and 10-11. In other words, the tibial tray 12, 12', 112, 212, 312, 412 and the stem 14, 14', 114, 214, 314, 414 are separate from each other. Thus, after the tibia T is surgically resected, a tibial tray 12, 12', 112, 212, 312, 412 is selected according to the size of the tibia T, and a stem 14, 14', 114, 214, 314, 414 is selected according to the size of the tibia T as well. Once the proper sizes have been identified, the tibial canal 50, 50', 50" is formed using the punch assembly 54, 554.

Then a "primary" tibial component 10, 10', 110, 210, 310, 410 is installed into the tibial canal 50, 50', 50" for use in the knee joint prosthesis. In some embodiments, the "primary" tibial component 10, 10', 110, 210, 310, 410 includes a tibial tray 12, 12', 112, 212, 312, 412 and a stem 14, 14', 114, 214, 314, 414 that are integrally attached.

Furthermore, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims.

What is claimed is:

1. A punch assembly for use in preparing a tibia bone with a tibia surface for a prosthesis comprising: a static component having a first surface configured to be supported on the tibia surface of the tibia bone and a second surface that is spaced apart from the first surface; a dynamic component that includes a punch having a stem, the dynamic component supported for sliding movement relative to the static component along a generally arcuate path extending between the first and second surfaces of the static component, wherein the static component includes an arcuate support surface that defines the generally arcuate path and includes a third surface that cooperates with the arcuate support surface to define a passage, wherein the third surface generally faces the arcuate support surface of the static component; the third surface is substantially flat, wherein the third surface is substantially parallel and disposed at a distance from an imaginary line that is substantially tangent to the arcuate support surface of the static component; and the dynamic component operable to bypass the static component and to penetrate the tibia surface as the dynamic component travels along the generally arcuate path into the tibia bone to prepare an aperture having an arcuate contour in the tibia bone.

2. The punch assembly of claim 1, wherein the stem has an arcuate contour.

3. The punch assembly of claim 1, wherein the stem includes at least one fin.

4. The punch assembly of claim 1, wherein the stem includes a plurality of teeth.

5. The punch assembly of claim 1, wherein the stem includes an arcuate support surface that corresponds in shape to the arcuate support surface of the static component, the arcuate support surface of the stem being supported for sliding movement against the arcuate support surface of the static component along the generally arcuate path.

6. The punch assembly of claim 1, wherein the generally arcuate path extends toward a generally posterior, inferior direction into the tibia bone.

7. The punch assembly of claim 1, further comprising a first handle that is removably coupled to the static component, the first handle including a grip portion defining a first axis and a coupling portion defining a second axis, wherein the coupling portion is removably coupled to the static component, and wherein the first axis is offset from the second axis.

8. The punch assembly of claim 1, further comprising a second handle that removably couples to the dynamic component and operable to extract the dynamic component from the tibia bone, wherein the static component is configured to be removably coupled to the tibia bone via a fastener, the second handle including a claw member that enables extraction of the fastener from the tibia bone.

9. The punch assembly of claim 1, wherein the dynamic component is configured to prepare the tibia bone for a knee joint prosthesis.

10. The punch assembly of claim 1, wherein the stem is generally cruciform in shape.

11. The punch assembly of claim 1, wherein the first surface of the static component is a bone engaging surface, and wherein the static component includes a fastener that is operable to extend from the bone engaging surface and into the tibia bone, the fastener disposed at a positive acute angle relative to the bone engaging surface.

12. The punch assembly of claim 1, further comprising a tibial tray with a tibial tray stem having a generally arcuate contour, the tibial tray stem operable to be received in the aperture prepared by the dynamic component.

13. A punch assembly for use in preparing a tibia bone with a tibia surface for a knee joint prosthesis comprising:
a static component having a first surface configured to be supported on the tibia surface of the tibia bone and a second surface that is spaced apart from the first surface, the static component defining a passage partially defined by a first arcuate support surface that defines a generally arcuate path between the first and second surfaces, the passage further defined by a third support surface that is substantially parallel and disposed at a distance from an imaginary line that is substantially tangent to the first arcuate support surface; and a dynamic component that includes a punch having a stem, the stem having a generally cruciform shape, an arcuate contour, a plurality of teeth, and a second arcuate support surface supported for sliding movement against the first arcuate support surface of the static component along the generally arcuate path to prepare an aperture having an arcuate contour in the tibia bone.

14. The punch assembly of claim 13, wherein the first surface of the static component is a bone engaging surface, and wherein the static component includes a fastener that is operable to extend from the bone engaging surface and into the tibia bone, the fastener operable to be disposed at a positive acute angle relative to the bone engaging surface.

15. The punch assembly of claim 13, further comprising a first handle that is removably coupled to the static component, the first handle including a grip portion defining a first axis and a coupling portion defining a second axis, wherein the coupling portion is removably coupled to the static component, and wherein the first axis is offset from the second axis.

16. The punch assembly of claim 13, further comprising a tibial tray with a tibial tray stem having a generally arcuate contour, the tibial tray stem operable to be received in the aperture prepared by the dynamic component.

17. The punch assembly of claim 13, further comprising a first handle that is removably coupled to the static component, the first handle including a grip portion defining a first axis and a coupling portion defining a second axis, wherein the coupling portion is removably coupled to the static component, and wherein the first axis is offset from the second axis, the punch assembly further comprising a second handle that removably couples to the dynamic component and operable to extract the dynamic component from the tibia bone, the second handle including a claw member that enables extraction of the fastener from the tibia bone.

18. A punch assembly for use in preparing a tibia bone for a knee joint prosthesis comprising:
  a static component that is configured to be removably coupled to the tibia bone via a fastener, the static component including a bone engaging surface, the fastener operable to be disposed at a positive acute angle relative to the bone engaging surface, the static component defining a passage partially defined by a first arcuate support surface that defines a generally arcuate path, the passage further defined by a third support surface that is substantially flat and that is substantially parallel and disposed at a distance from an imaginary line that is substantially tangent to the first arcuate support surface;
  a dynamic component that includes a punch having a stem, the stem having a generally cruciform shape, an arcuate contour, a plurality of teeth, and a second arcuate support surface supported for sliding movement against the first arcuate support surface of the static component along the generally arcuate path to prepare an aperture having an arcuate contour in the tibia bone;
  a first handle that is removably coupled to the static component, the first handle including a grip portion defining a first axis and a coupling portion defining a second axis, wherein the coupling portion is removably coupled to the static component, and wherein the first axis is offset from the second axis; and
  a second handle that removably couples to the dynamic component and operable to extract the dynamic component from the tibia bone, the second handle including a claw member that enables extraction of the fastener from the tibia bone.

* * * * *